United States Patent [19]

Karczewski

[11] Patent Number: 4,651,722

[45] Date of Patent: Mar. 24, 1987

[54] KNEE SUPPORT STRUCTURE

[76] Inventor: Robert A. Karczewski, P.O. Box 202, Falmouth, Mass. 02541

[21] Appl. No.: 755,279

[22] Filed: Jul. 15, 1985

[51] Int. Cl.⁴ .............................................. A61F 3/00
[52] U.S. Cl. ................................................. 128/80 C
[58] Field of Search ................. 128/80 C, 80 F, 80 R, 128/88

[56] References Cited

U.S. PATENT DOCUMENTS

| | | | |
|---|---|---|---|
| 3,677,265 | 7/1972 | Brabazon | 128/80 C |
| 4,064,874 | 12/1977 | Valin | 128/80 C |
| 4,130,115 | 12/1978 | Taylor | 128/80 C |
| 4,144,881 | 3/1979 | Chappell | 128/80 F X |
| 4,366,813 | 1/1983 | Nelson | 128/80 C |
| 4,445,505 | 5/1984 | Labour et al. | 128/80 C |
| 4,474,573 | 10/1984 | Detty | 128/80 C |

Primary Examiner—Clifford D. Crowder
Attorney, Agent, or Firm—Cesari and McKenna

[57] ABSTRACT

A reusable knee support structure comprises an inner layer of a resilient material, such as neoprene rubber, and an outer layer of a relatively non-resilient but flexible material, such as Dacron ® sail cloth, that is secured as a pair of mirror image sections to the outside surface of the inner layer. A pair of articulated linkages, each made of a material such as roller or bicycle chain, is disposed between the inner and outer layers on each side of the center line of the support structure. The resilient layer is snugly wrapped around the knee of a human with an aperture in the inner layer positioned over the kneecap. Hook and loop fastening panels may be secured to the structure to facilitate its application.

20 Claims, 4 Drawing Figures

KNEE SUPPORT STRUCTURE

BACKGROUND OF THE INVENTION

This invention relates to a support structure for a body member and, more particularly, to a reusable support structure for the knee joint of a human.

The human knee is commonly considered a hinged joint performing two principal actions, flexion and extension. The anatomical structure of the knee joint consists primarily of the joining of the femur bone with the tibia bone. This is accomplished by several articulations including: an articulation between two positions on the femur and two corresponding semilunar cartilages called menisci; are between the tibia and the menisci; and are between a piece of cartilage known as the patella or kneecap. Ligaments stabilize the knee at these articulations both laterally and medially.

Knee injuries are common among humans engaging in athletic and other strenuous activities. Injuries result because the bone-cartilege-ligament arrangement of the knee is relatively weak in face of forces applied medially, laterally, and rotationally. The injuries from these forces vary widely in severity from bruising tissues around the knee, simple ligament pulls or sprains and cartilage dislocations to ligament and cartilage tears and ruptures.

Compression or contusion type injuries result from falling or receiving a direct blow to either side of the knee joint. Lateral and medial sprains and tearing of the lateral and medial supporting ligament of the knee result generally from the receipt of a direct blow to the lateral or medial portion of the knee, while the foot appended thereto is firmly planted. Torsion type injuries result from an abnormal wrenching of the knee joint, usually when a foot is planted in one position, while above the knee the upper portion of the body is forced to move to a different position.

For individuals, particularly athletes and others, who have had a history of weak or injured knees, the common practice has been to tape their knees with medical adhesive tape. This suffers from a number of drawbacks. Tape is not reusable and thus is relatively expensive, particularly where frequent applications are required. Tape also generally requires a second person to apply it. Some skill and expertise on the part of the person applying the tape is also generally required, as improper application can cause reinjury, exacerbation of the existing injury, blood circulation problems, or irritation or cutting of the skin area under the tape. Moreover, the use of the tape to prevent medial and lateral movement of the knee inhibits the normal flexion and extension of the knee joint.

Because of these short-comings, reusable fabric knee wraps have been used in place of taping. However, wraps by themselves cannot give the support provided by properly applied tape. Typically, wraps and the wrap material slip relative to the skin. Such slippage results in loosening of the wrap and generally in the loss of the benefits provided by the wrap.

Further, various stays or other mechanical devices have been used in conjuntion with both medical taping and wraps, as a means to provide increased stability and rigidity. These devices vary widely in use and structure. Most of the simpler devices provide no real support against lateral and medial movement of the knee while also providing full flexion and extension range for the knee. The more complicated devices are generally more effective in this regard although typically they are expensive, cumbersome, and difficult for an individual to position and apply the knee support to his or her own knee.

OBJECTS OF THE INVENTION

It is, therefore, a primary object of this invention to provide an improved support structure for a body member such as a human knee.

Another object of the invention is to provide a knee support structure that has a relatively simple and inexpensive construction and that is reusable.

Another object of the invention is to provide a knee support structure of the type described that provides effective support against injury, including contusions and compression injuries, lateral and medial sprains and torsion type injuries, but allows essentially free flexion and extension of the knee.

Another object of the invention is to provide a knee support of the type described that can be applied by an individual to his or her own knee with relative ease.

Another object of the invention is to provide a knee support structure of the type described, that, when applied to the knee, serves to retain body heat in the knee thus keeping the knee tissues, muscles, ligaments and the like warm and flexible.

A further object of the invention is to provide a knee support structure of the type described, that, when applied to a post-injured knee, provides lateral and medial stailization of the knee while allowing essentially free flexing and extending of the knee whereby the post-injured knee functions as an essentially normal knee, while still affected by the injury.

Still another object of the invention is to provide a knee support structure of the type described that, when applied to the knee, resists slippage relative to the skin and thus tends to maintain its support position for longer periods of time.

SUMMARY OF THE INVENTION

Briefly, a knee support structure fabricated in accordance with the invention comprises an outer, relatively non-resilient but flexible layer, and an inner, knee enveloping layer of a relatively resilient material that is secured to the inside surface of the outer layer. Disposed between the inner and outer layers of the support structure are articulated linking means which readily bend and flex within the plane of the two layers but which resists bending or flexing out of the plane of the two layers.

The inner layer of the support structure is dimensioned so that it can be snugly wrapped completely around the knee and suitably secured there. The articulated linking means are dimensioned and positioned so that they are disposed on opposite sides of the knee and are articulated in the direction of flexion and extension of the knee and essentially rigid in other directions. The articulated linking means thus provide a rigid support that resists external forces due to twisting, turning, and other abnormal knee movements while providing for essentially normal freedom to flex and extend the knee joint.

In a preferred embodiment of the invention, panels of hook and loop fastening material are secured at various locations on the support structure to facilitate application of the structure and make it possible for an individual to apply the structure to his or her own knee with relatively little effort. The fastening panels are of sufficient size to permit adjustment of the structure so that each individual can achieve a snug, but comfortable fit. The outer layer is preferably formed from a cloth fabric, such as dacron sail cloth, which is both strong, durable and washable, and in two separate sections so as not to unduly limit the resiliency of the inner layer. The inner layer is preferably formed from material, such as neoprene rubber, that resiliently envelopes the knee and clings to the skin thus avoiding loosening of the structure on the knee. The neoprene rubber layer also has therapeutic value in that it retains body heat in the knee which keeps the knee warm and flexible, thus helping to prevent further injury while promoting increased circulation and healing.

BRIEF DESCRIPTION OF THE DRAWINGS

The foregoing and other objects, features and advantage of the invention will be better understood from the following detailed description taken in conjunction with the accompanying drawings in which.

DETAILED DESCRIPTION OF THE PREFERRED EMBODIMENTS

Figure 1:
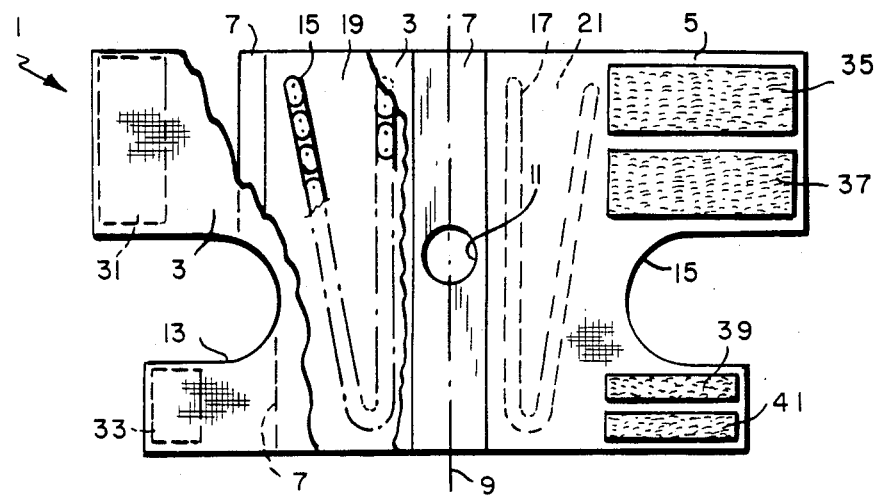
FIG. 1 is a pictorial view of the outside surface of a knee support structure embodying the invention with a portion broken away.
Figure 2:
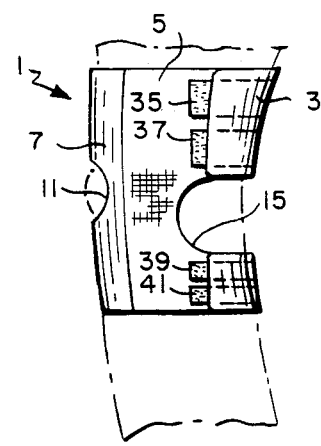
FIG. 2 is a pictorial view of the knee support structure secured around a knee.

Referring now specifically to FIGS. 1 and 2, they show a support structure 1 embodying the invention adapted for application to the knee of a human. The structure 1 comprises two outer layer sections 3 and 5, secured to an inner layer 7 which is exposed between sections 3 and 5. Inner layer 7 is formed of a relatively resilient material, such as neoprene rubber, and is dimensioned and shaped to resiliently envelope the knee in the manner shown in FIG. 2 and described more fully below.

As best seen in FIG. 1, the outer sections 3 and 5 are preferably shaped in a mirror image and positioned on the inner layer 7 in a symmetrical fashion. Inner layer 7 is preferably formed in a single piece that is essentially symmetrical in shape above a center line 9 except for the fact that the layer 7 extends to the extreme end of section 5 but does not extend to the extreme end of section 3. This difference in the opposite sides of layer 7 tends to avoid overlap of the ends of layer 7 when the structure 1 is wrapped about a knee.

Sections 3 and 5 may be secured to the inner layer 7 in any suitable manner. A high strength rubber bond adhesive, for example, has been used for this purpose. The adhesive used preferably is one that stays relatively flexible and resilient when dry. Further, the fact that the sections 3 and 5 leave the central portion of inner layer 7 exposed further adds to the resiliency of the structure 1, since in this region the inner layer 7 is free of the constraints due to the bonding to the sections 3 and 5.

An aperture 11 extends through the layer 7 between sections 3 and 5. The aperture 11 is adapted to expose the kneecap and to provide a more comfortable, less irritating fit at that location. The aperture 11, by straddling the kneecap, also serves to resist slipping and twisting of the layer 7 on the knee, as well as providing a positioning guide for application of the structure.

Corresponding J-shaped cuts 13, 15 in the outer layers 3 and 5 and the left hand side of the inner layer 7 facilitate the flexion and extension functions of the support structure 1. Thus, when a knee is wrapped with the structure 1, a void is created along the rearward face of the knee. This provides greater freedom of movement as well as a less irritating and more comfortable fit at the rearward face of the knee, since there is no material to bind or inhibit normal movement.

Two articulated linking means 15 and 17 are provided in a pocket formed between section 3 and layer 7, and between section 5 and layer 7, respectively. Two inserts 19 and 21 sized slightly larger than the articulated linking means 15 and 17 are secured on one face to the layer 7 in any suitable manner, for example, through the use of a high strength rubber bond adhesive, while the other face of each insert 19 and 21 is exposed to the articulated linking means 15 and 17. The inserts 19 and 21 are formed of a relatively resilient material, such a neoprene rubber, and act in conjunction with layer 7 as a pad between the knee and the articulated means 15 and 17 positioned on each of the inserts 19 and 21 respectively.

The articulated linking means 15 and 17 are preferably formed of a material that flexes and extends in the plane of the layers 3, 5, and 7 while remaining relatively rigid and providing support against twisting, turning and lateral movements out of that plane. A roller chain, and particularly a bicycle chain, have been found to be admirably suited for this purpose. When such a chain is secured in the pockets as shown at 15 and 17 in FIG. 1, with its longitudinal axis extending generally parallel to the axis of the leg, the chain readily bends and flexes in the direction of normal knee movement, yet provides rigid support against blows to the side of the knee and resists twisting, wrenching, and turning of the knee.

As noted, a high strength rubber bond adhesive may be used to secure the articulated linking means 15 and 17 in the structure 1. Alternatively, the means 15 and 17 may be secured by merely sewing portions of them to the inner layer 7 and to the corresponding outer sections, or by constructing an envelop (not shown) in the pockets which is sized to approximate the shape of the articulated means 15 and 17 such that each is held in such an envelop yet may move longitudinally therein without twisting or turning.

Panels 31, 33, 35, 37, 39 and 41 of hook and loop fastening material are the type available commercially under the trademarks Velcro ® or Gripper ® strip may be secured to various parts of the structure 1 for use in securing the structure 1 to the knee. For example, the panels 31 and 33, which are secured to the inside of the outer layer section 3, may be formed of loop material. The panels 35, 37, 39 and 41, which are secured to the outside surface of section 5, may be formed of hook material. The panels 31, 35 and 37 thus cooperate in securing the upper portion of inner layer 7 around the knee. Likewise, panels 33, 39 and 41 cooperate in securing the lower portion of inner layer 7 around the knee. Each of the panels 31, 33, 35, 37, 39 and 41 may be fixed in place by any suitable means, such as by stitching or adhesive.

The structure 1 is applied to the knee in the following manner. The center inside surface of the inner layer 7 is brought to bear against the front of the knee with the aperture 11 positioned about the kneecap. The sections 3 and 5 are then gripped, wrapped toward the rear of the knee, and pulled together to stretch the inner layer 7 around the knee, so as to achieve a snug but comfortable grip around the knee. Section 3 is then disposed over section 5 and panels 31 and 33 are pressed against panels 35 and 37 and panels 39 and 41 respectively to secure the structure 1 in place. A single strip of medical adhesive tape may be wrapped around the structure 1, above and below the kneecap, to ensure against relative loosening of panels 31, 33, 35, 37, 39 and 41 during use.

Figures 3, 4:
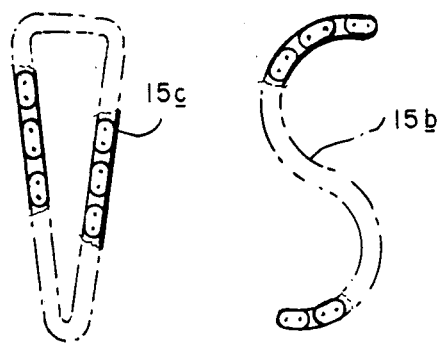
FIG. 3 is a pictorial view showing an alternative embodiment of the articulated linking means structure.
FIG. 4 is a pictorial view showing another embodiment of the articulated linking means structure.

Referring now to FIG. 3, an ovoid-shaped articulated linking means 15C, again preferably of bicycle chain, is shown with both ends joined together, which may also be used as an alternative to the configuration shown in FIG. 1. Likewise, in FIG. 4, an S-shaped articulated linking means 15B, preferably made of bicycle chain, is shown, which may be used as an alternative to the V-shaped articulated linking means shown in FIG. 1. These various configurations may provide increased support for a particular type of injury while still providing the general benefits discussed above in connection with the embodiment of FIGS. 1 and 2.

In summary, it can be seen that the above described knee support structure 1 possesses several attractive features. For example, the structure 1 has a simple, low-cost construction which, when combined with its reuseability and durability, makes it an economically attractive alternative to taping. The structure 1 is simple enough to apply that an individual can readily apply it to his or her own knee. Although various different sizes of the structure 1 may be necessary to accommodate the broad spectrum of knee sizes for children, adult females, and adult males, each structure will provide considerable room for adjustment, thus enabling the individual to achieve the fit that best suits him or her. Additionally, and perhaps most importantly, the structure 1 provides effective support against the most common cause of knee injuries but does not unnecessarily interfere with the free use of the knee.

There are also other advantages that result from the use of the material such as neoprene rubber for the inner layer 7. The surface texture of this material is such that it clinges to the skin around the knee even as the skin in that region begins and continues to perspire. Consequently, the inner layer 7 holds fast to the region around the knee where it is mounted and does not loosen after long use of said structure 1 once it is secured around the knee. The material also tends to insulate the area around which it is mounted and retain the body heat generated in the region. This heat not only keeps the muscles, ligaments, and the like warm and flexible which aids in resisting pulls and tears and reinjury, but retention of this heat also promotes the healing and increased circulation to the injured areas.

It should also be understood that the above-described knee support structure 1 is intended to illustrate rather than limit the invention and that numerous modifications can be made thereto without departing from the scope of the invention as defined by the appended claims. For example, the outer layer sections 3 and 5 can be formed from a material such as rubberized fabric, that itself has resiliency and elasticity. The outer layers may be in the form of a single continuous layer that extends completely across the outside surface of the inner layer 7 rather than in the form of two separate sections 3 and 5. Also, to provide even greater support for the knee, additional articulated linking means may be secured within the structure 1. For example, it may be desirable in some cases to secure a third and even fourth articulated linking means of the same or even different configuration between inner layer 7 and the seperate sections 3 and 5. Likewise, to provide further padding between the knee and the articulated linking means additional inserts may be disposed as further buffering pads.

It is thus the object of the appended claims to cover these and other modifications as come within the true spirit and scope of the invention herein disclosed.

What is claimed as new and desired to be secured by Letters Patent of the United States is:

1. A reusable support structure for application to the knee of a human comprising:
   A. an inner layer
      i. formed of a relatively resilient material,
      ii. having dimensions that enable said layer to be resiliently wrapped around the knee, and
      iii. having an inside surface for facing inwardly against the knee and an outside surface;
   B. an outer layer
      i. comprising first and second separate, essentially mirror image sections secured in spaced apart positions to the outside surface of said inner layer, and
      ii. each of said outer layer sections being formed of a relatively non-resilient flexible material; and
   C. articulated linking means
      i. positioned between said inner layer and one of said separate outer layers, and
      ii. being secured within said structure such that said means are relatively inflexible to twisting and lateral forces applied to it while providing for relatively free flexing and extension of the knee.

2. A support structure as recited in claim 1, further comprising an aperture in said inner layer sized for positioning over the kneecap 3. A support structure as recited in claim 2, wherein said inner layer includes first and second opposed side members, in which said first side member extends outwardly from the center of said inner layer through a greater distance than said second side member, in which said first and second outer layers are secured over said first and second inner layers, respectively, such that a portion of said second outer layer extends beyond the end of said second inner layer, the extended portion of said second outer layer overlaps said first outer layer when said inner layer is wrapped around the knee.

4. A support structure as recited in claim 3, wherein said articulated linking means are two articulated linking means disposed on opposite sides of said knee.

5. A support structure as recited in claim 2 wherein said aritculated linking means are two roller chains having relatively small, uniformly sized links and positioned on opposite sides of the knee.

6. A support structure as recited in claim 5, wherein said chains are positioned between said layers in a V-shape.

7. A support structure as recited in claim 1, further comprising a resilient internal layer positioned between said articulated linking means and said inner layer; said articulated linking means being secured to said internal layer which is in turn secured to said inner layer, said internal layer thereby providing further padding for the knee.

8. A support structure as recited in claim 1 further comprising a fastening panel of a first type secured to said first separate outer layer section and a fastening panel of a second, cooperating type secured to said second separate outer layer section for removably securing said structure around said knee.

9. A support structure as recited in claim 1 in which said inner layer is formed from neoprene rubber.

10. A support structure as recited in claim 1 in which said outer layer sections are formed of Dacron ® sailcloth.

11. A support structure as recited in claim 1 wherein said articulated linking means are two roller chains positioned on opposite sides of the kneecap.

12. A support structure as recited in claim 11 wherein said roller chains have two flat sides which are positioned so that one of their flat sides face the inner layer while their other flat sides face the outer layer.

13. A reusable support structure for application to a knee of a user comprising:
an inner layer having dimensions that enable said layer to be wrapped around the knee of the user, said inner layer having an inside surface adapted to face inwardly against the knee and an outer surface, an outer layer centered about the kneecap secured to said inner layer, a roller chain and having a plurality of relatively small, uniformly sized linkages, said chain being disposed between said inner and outer layers and positioned on one side of the knee, and means for securing said structure around the knee.

14. A support structure as recited in claim 13, wherein said roller chain is positioned between said layers in a Z-shaped fashion.

15. A support structure as recited in claim 13, wherein said chain is positioned between said layers in a S-shaped fashion.

16. A support structure as recited in claim 13, wherein said chain is positioned between said layers in an oviod-shaped fashion.

17. A support structure as recited in claim 13, further comprising a second roller chain having a plurality of relatively small, uniformly sized linkages, said second roller chain being disposed between said inner and outer layers and positioned on the opposite side of the knee from said first-named chain.

18. A support structure as recited in claim 13, wherein said outer layer is formed of a non-resilient, flexible material.

19. A support structure as recited in claim 18, wherein said inner layer is formed of a resilient material.

20. A support structure as recited in claim 18, wherein said structure defines an aperture disposed such that it is adapted for positioning at the back of the knee.

* * * * *